(12) United States Patent
Cho et al.

(10) Patent No.: US 12,419,757 B2
(45) Date of Patent: Sep. 23, 2025

(54) SPINAL CAGE

(71) Applicant: KYUNGPOOK NATIONAL UNIVERSITY INDUSTRY-ACADEMIC COOPERATION FOUNDATION, Daegu (KR)

(72) Inventors: Dae-Chul Cho, Daegu (KR); Gunwoo Noh, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 240 days.

(21) Appl. No.: 17/927,161

(22) PCT Filed: May 21, 2021

(86) PCT No.: PCT/KR2021/006309
§ 371 (c)(1),
(2) Date: Nov. 22, 2022

(87) PCT Pub. No.: WO2022/010093
PCT Pub. Date: Jan. 13, 2022

(65) Prior Publication Data
US 2023/0190486 A1 Jun. 22, 2023

(30) Foreign Application Priority Data
Jul. 10, 2020 (KR) .................... 10-2020-0085467

(51) Int. Cl.
*A61F 2/44* (2006.01)
*A61F 2/30* (2006.01)

(52) U.S. Cl.
CPC .... *A61F 2/442* (2013.01); *A61F 2002/30014* (2013.01); *A61F 2002/30069* (2013.01);
(Continued)

(58) Field of Classification Search
CPC .. A61F 2/442; A61F 2/4425; A61F 2002/443; A61F 2002/4435
See application file for complete search history.

(56) References Cited

U.S. PATENT DOCUMENTS 5,674,294 A * 10/1997 Bainville ................ A61F 2/442
623/17.16
8,696,749 B2 * 4/2014 Lyons ..................... A61F 2/442
623/17.15
(Continued)

FOREIGN PATENT DOCUMENTS

CN 202211766 U 5/2012
CN 106264804 B 12/2019
(Continued)

*Primary Examiner* — Eduardo C Robert
*Assistant Examiner* — Anna V. Little
(74) *Attorney, Agent, or Firm* — NKL Law; Jae Youn Kim

(57) ABSTRACT

Proposed is a spinal cage. The spinal cage includes a bone support portion configured to be disposed between a first vertebra at an upper side and a second vertebra at a lower side to support the first vertebra, a base portion positioned at a lower side of the bone support portion to come in contact with the second vertebra, and a sidewall portion which has an upper side end connected to an edge of the bone support portion and a lower side end connected to an edge of the base portion and includes an elastic band having elasticity and inelastic bands having relatively lower elasticity or no elasticity. Therefore, subsidence of the spinal cage into vertebrae can be suppressed.

6 Claims, 10 Drawing Sheets

(52) U.S. Cl.
CPC .............. *A61F 2002/30563* (2013.01); *A61F 2002/4495* (2013.01)

(56) References Cited

U.S. PATENT DOCUMENTS

| | | | |
|---|---|---|---|
| 2003/0045939 A1* | 3/2003 | Casutt | A61F 2/442 623/17.15 |
| 2004/0102849 A1 | 5/2004 | Ralph et al. | |
| 2006/0052871 A1* | 3/2006 | Studer | A61F 2/44 623/17.13 |
| 2010/0070033 A1* | 3/2010 | Doty | A61F 2/4425 623/17.14 |
| 2011/0196495 A1 | 8/2011 | Hunt | |
| 2014/0058517 A1* | 2/2014 | Sabatino | A61F 2/4425 623/17.16 |
| 2017/0156878 A1 | 6/2017 | Tsai et al. | |
| 2018/0256336 A1 | 9/2018 | Mueller et al. | |
| 2019/0000636 A1* | 1/2019 | Kim | A61F 2/447 |
| 2019/0133783 A1 | 5/2019 | Unger et al. | |
| 2020/0046512 A1* | 2/2020 | Newman | A61F 2/442 |

FOREIGN PATENT DOCUMENTS

| | | | |
|---|---|---|---|
| CN | 210644254 U | 6/2020 | |
| JP | 2009-506843 A | 2/2009 | |
| KR | 10-1326054 B1 | 11/2013 | |
| KR | 10-2016-0128236 A | 11/2016 | |
| WO | WO-2013085881 A1 * | 6/2013 | ........... A61F 2/4425 |

\* cited by examiner

SPINAL CAGE

TECHNICAL FIELD

The present disclosure relates to a spinal cage insertable between vertebrae to support the vertebrae.

BACKGROUND ART

Intervertebral discs serve as joints, and a nucleus pulposus located in the center of each disc changes its position and shape with movement of the spine, thereby playing an important role of minimizing impact applied to the spine.

As a method of treating a disease involving a disc, there is a method of treatment in which a disc between damaged vertebrae is removed, and then a space between two adjacent vertebrae is replaced with a prosthetic material such as a cage. The cage helps restore an original distance between two adjacent vertebral bodies, which is an original height of the intervertebral disc, to restore the functions of the spine.

The cage has a solid structure made of a metal material such as titanium or a titanium alloy, and sometimes, a problem occurs in which, after the cage is inserted between a vertebra and a neighboring vertebra and surgery is completed, surfaces of the vertebra and the neighboring vertebra that face each other subside due to an upper surface and a lower surface of the cage.

That is, there is a problem in which, when pressure and impact according to a patient's weight and posture changes are not properly absorbed, an upper side surface or a lower side surface of a cage inserted between a vertebra and another neighboring vertebra subsides into the vertebrae.

RELATED ART DOCUMENT

Patent Document (Patent Document 1) Korean Patent Publication no. 10-2016-0128236

DISCLOSURE

Technical Problem

The present disclosure provides a spinal cage which can suppress subsidence of a spinal cage insertable between vertebrae into the vertebrae.

Technical Solution

One embodiment of the present disclosure provides a spinal cage including: a bone support portion disposed between a first vertebra at an upper side and a second vertebra at a lower side, which neighbor each other, to support the first vertebra; a base portion positioned at a lower side of the bone support portion and disposed between the first vertebra and the second vertebra to come in contact with the second vertebra; and a sidewall portion which has an upper side end connected to an edge of the bone support portion and a lower side end connected to an edge of the base portion to support the bone support portion relative to the base portion and which includes an elastic band having elasticity and inelastic bands having relatively lower elasticity than the elastic band or no elasticity.

Here, in the sidewall portion, the inelastic bands may include a first inelastic band which has an upper side connected to the edge of the bone support portion and a lower side connected to the elastic band and a second inelastic band which has an upper side connected to the elastic band and a lower side connected to the edge of the base portion, and the elastic band may be positioned between the first inelastic band and the second inelastic band and be elastically deformable corresponding to a pressure between the first vertebra and the second vertebra.

Here, the elastic band may have a form in which a cross-sectional thickness gradually increases from a center of the elastic band toward an edge thereof.

Here, the first inelastic band and the second inelastic band may be formed so that elasticity gradually decreases from the elastic band toward the bone support portion or the base portion.

Here, the elastic band may be an assembly formed by a consecutive connection of a plurality of elastic unit bodies which are elastically deformable corresponding to an external force.

Here, the elastic unit body may be deformable according to the external force and may include a plurality of struts connecting vertices and crossing points of a virtual hexahedron, and the crossing points may be points provided at positions spaced apart at predetermined intervals inward of the virtual hexahedron at a face-centered of the virtual hexahedron.

Here, the strut of the elastic unit body may have an arch shape or a curved shape.

Here, the elastic unit body may include a base beam which has one side end positioned on a vertex of a virtual hexahedron and is formed to have a predetermined length in a height direction, an impact absorbing beam which has one side end connected to the other side end of the base beam, forms an acute angle relative to the base beam, and is formed to have a predetermined length, and a support beam which has one side end connected to the other side end of the impact absorbing beam and the other side end connected to one side end of another impact absorbing beam to have a predetermined length and which has a longitudinal direction parallel to the base beam.

Here, the elastic unit body may include a base beam which has one side end positioned on a vertex of a virtual hexahedron and is formed to have a predetermined length in a height direction, an impact absorbing beam which has one side end connected to the other side end of the base beam, forms an acute angle relative to the base beam, and is formed to have a predetermined length, a support beam which has one side end connected to the other side end of the impact absorbing beam and the other side end connected to one side end of another impact absorbing beam to have a predetermined length and which has a longitudinal direction parallel to the base beam, and a torsion beam formed to have a predetermined length in a direction perpendicular to a longitudinal direction of the base beam or the longitudinal direction of the support beam, wherein the torsion beam has one side end connected to the other side end of the base beam and the other side end connected to one side end of another base beam or has one side end connected to the one side end of the support beam and the other side end connected to one side end of another support beam.

Advantageous Effects

A spinal cage according to an embodiment of the present disclosure has an effect of relieving pressure between vertebrae and suppressing an occurrence of subsidence.

MODES OF THE INVENTION

Figure 1:
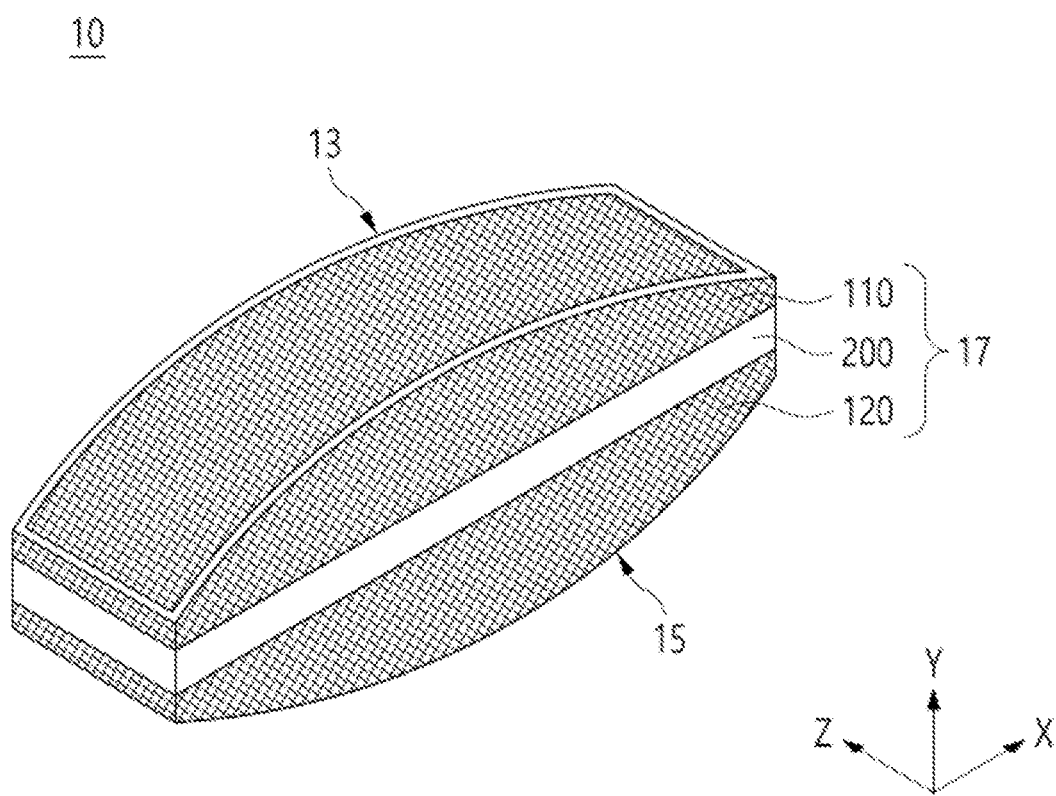
FIG. 1 is a perspective view schematically illustrating a spinal cage according to an embodiment of the present disclosure.

Hereinafter, exemplary embodiments will be described with reference to the accompanying drawings to facilitate understanding of the present disclosure.

Since various modifications may be made to the present disclosure and the present disclosure may have various embodiments, specific embodiments illustrated in the drawings will be described in detail. However, this does not limit the present disclosure to the specific embodiments, and all modifications, equivalents, and/or substitutes included in the spirit and technical scope of the present disclosure should be construed as belonging to the present disclosure.

Terms such as "first" and "second" may be used to describe various elements, but the elements are not limited by the terms. The terms are only used for the purpose of distinguishing one element from another element. For example, a first element may be referred to as a second element while not departing from the scope of the present disclosure, and likewise, a second element may also be referred to as a first element. The term "and/or" includes a combination of a plurality of associated listed items or any one item among the plurality of associated listed items.

When it is mentioned that a certain element is "connected" or "linked" to another element, although the certain element may be directly connected or linked to the other element, it should be understood that another element may be present therebetween. On the other hand, when it is mentioned that a certain element is "directly connected" or "directly linked" to another element, it should be understood that other elements are not present therebetween.

Terms used in the application are merely used to describe particular embodiments and are not intended to limit the present disclosure. A singular expression includes a plural expression unless the context clearly indicates otherwise. In the application, terms such as "include" or "have" should be understood as specifying that features, number, steps, operations, elements, components, or combinations thereof are present and not as precluding the possibility of the presence or addition of one or more other features, numbers, steps, operations, elements, components, or combinations thereof in advance.

Unless otherwise defined, all terms including technical or scientific terms used herein have the same meaning as commonly understood by one of ordinary skill in the art to which the present disclosure pertains. Terms, such as those defined in commonly used dictionaries, should be construed as having a meaning that is consistent with their meaning in the context of the relevant art and are not to be construed in an idealized or overly formal sense unless expressly so defined herein.

Hereinafter, exemplary embodiments of the present disclosure will be described in more detail with reference to the accompanying drawings. In describing the present disclosure, in order to facilitate overall understanding, the same elements will be denoted by the same reference numerals throughout the drawings and repeated descriptions thereof will be omitted.

FIG. 1 is a perspective view schematically illustrating a spinal cage according to an embodiment of the present disclosure. Referring to FIG. 1, a spinal cage 10 according to an embodiment of the present disclosure includes a bone support portion 13, a base portion 15, and a sidewall portion 17.

The bone support portion 13 is configured to be disposed between a first vertebra at an upper side and a second vertebra at a lower side, which neighbor each other, to support the first vertebra. The bone support portion 13 may have a mesh-like form.

The base portion 15 is positioned at a lower side of the bone support portion 13 and disposed between the first vertebra and the second vertebra to come in contact with the second vertebra. Also, the base portion 15 may have a mesh-like form.

The sidewall portion 17 is connected to the bone support portion 13 and the base portion 15 between the bone support portion 13 and the base portion 15 and serves to support the bone support portion 13 based on the base portion 15.

That is, as can be seen from the drawing, the sidewall portion 17 has an upper side end connected to an edge of the bone support portion 13. Also, a lower side end of the sidewall portion 17 is connected to an edge of the base portion 15 to support the bone support portion 13 relative to the base portion 15.

The sidewall portion 17 includes an elastic band 200 having elasticity and inelastic bands 110 and 120 having relatively lower elasticity than the elastic band 200 or no elasticity.

As can be seen from FIG. 1, the sidewall portion 17 may include the single elastic band 200 and the two inelastic bands 110 and 120. Here, the two inelastic bands 110 and 120 are a first inelastic band 110 and a second inelastic band 120, which are only differentiated for convenience of description and are substantially the same.

The first inelastic band 110 has an upper side connected to the edge of the bone support portion 13 and a lower side connected to the elastic band 200.

The second inelastic band 120 has an upper side connected to the elastic band 200 and a lower side connected to the edge of the base portion 15.

Also, the elastic band 200 is positioned between the first inelastic band 110 and the second inelastic band 120. The elastic band 200 may be elastically deformable corresponding to a pressure between the first vertebra and the second vertebra.

Figure 2:
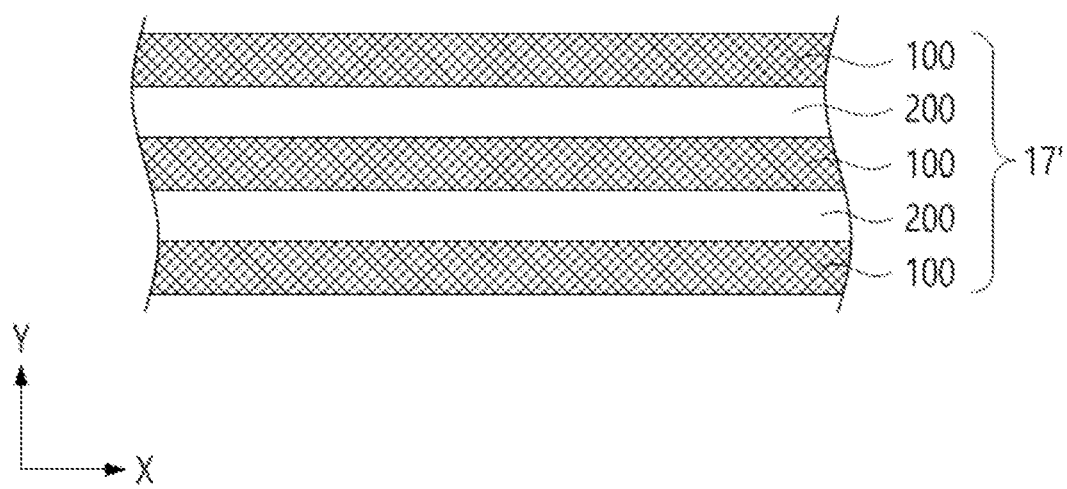
FIG. 2 is a lateral view schematically illustrating another exemplary form of the spinal cage according to an embodiment of the present disclosure.

In this way, the sidewall portion 17 may have a form in which the first inelastic band 110 is positioned at an upper side and the second inelastic band 120 is positioned at a lower side while the single elastic band 200 is present therebetween or may also have a form which can be seen from FIG. 2.

FIG. 2 is a lateral view schematically illustrating another exemplary form of the spinal cage according to an embodiment of the present disclosure.

Referring to FIG. 2, a sidewall portion 17' includes a plurality of inelastic bands 100 and a plurality of elastic bands 200.

Here, the plurality of inelastic bands 100 and the plurality of elastic bands 200 may be alternately arranged with each other in a vertical direction as can be seen from FIG. 2 and help elastically absorb pressure between the vertebrae.

Also, further reference will be made to FIGS. 3A and 3B, in addition to FIG. 1, for description of a cross-sectional shape of the sidewall portion.

Figure 3A:
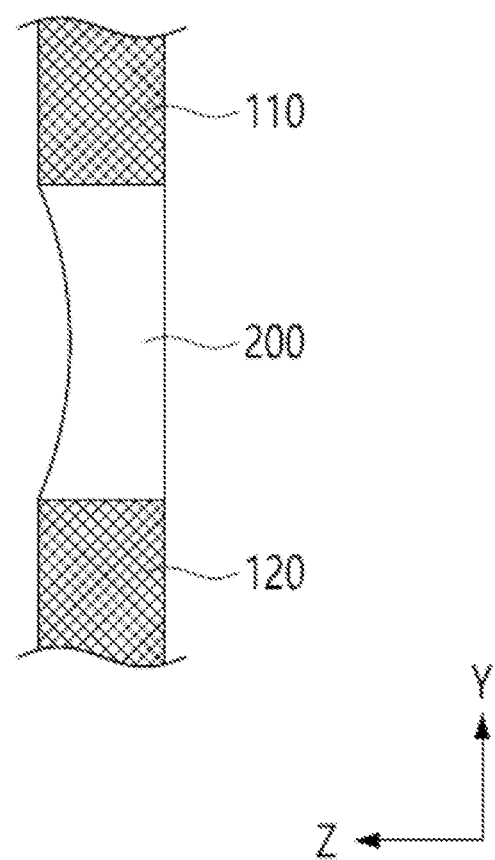
FIGS. 3A and 3B are plan views schematically illustrating a cross-section of a sidewall portion of the spinal cage according to an embodiment of the present disclosure.
Figure 3B:
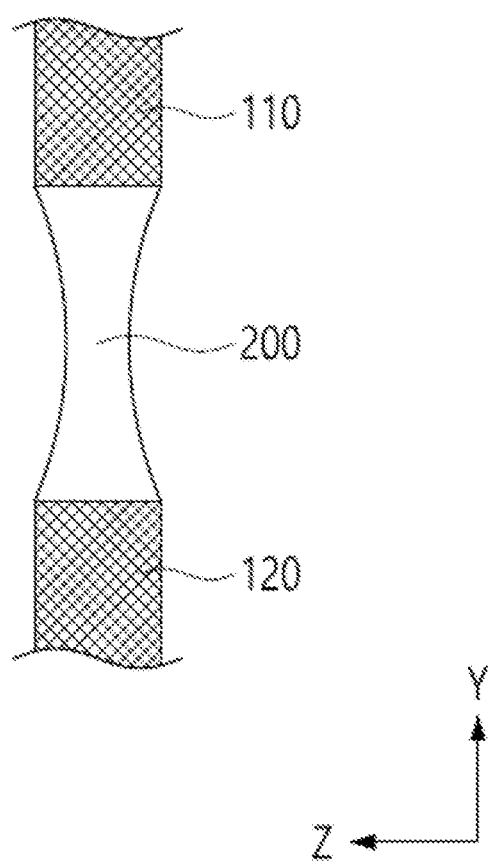

FIGS. 3A and 3B are plan views schematically illustrating the cross-section of the sidewall portion of the spinal cage according to an embodiment of the present disclosure.

As can be seen from FIGS. 1 and 3A, the elastic band 200 may have a form in which a cross-sectional thickness gradually increases from a center of the elastic band 200 toward an edge thereof, that is, toward the first inelastic band 110 or the second inelastic band 120.

In other words, a thickness of the center of the elastic band 200 may be formed to be smaller than a thickness of an edge thereof.

Therefore, as the cross-sectional shape of the elastic band 200, a shape in which one side is formed to be concave as illustrated in FIG. 3A is possible, and as the lateral cross-sectional shape of the elastic band 200, a shape in which both sides are formed to be concave as in a concave lens as illustrated in FIG. 3B is also possible.

In this way, an elastic force of the elastic band 200 may be adjusted and formed by adjusting the thickness of the elastic band 200.

Meanwhile, the first inelastic band 110 and the second inelastic band 120 may be formed so that elasticity gradually decreases from the elastic band 200 toward the bone support portion 13 or the base portion 15.

For example, the elasticity of the first inelastic band 110 and the second inelastic band 120 may gradually decrease due to the thickness thereof gradually increasing from the elastic band 200 toward the bone support portion 13 or the base portion 15.

For reference, such differences in the thicknesses of different portions of the elastic band 200 may also be applied to the form of the elastic bands 200 of the sidewall portion 17' described above with reference to FIG. 2.

Figure 4:
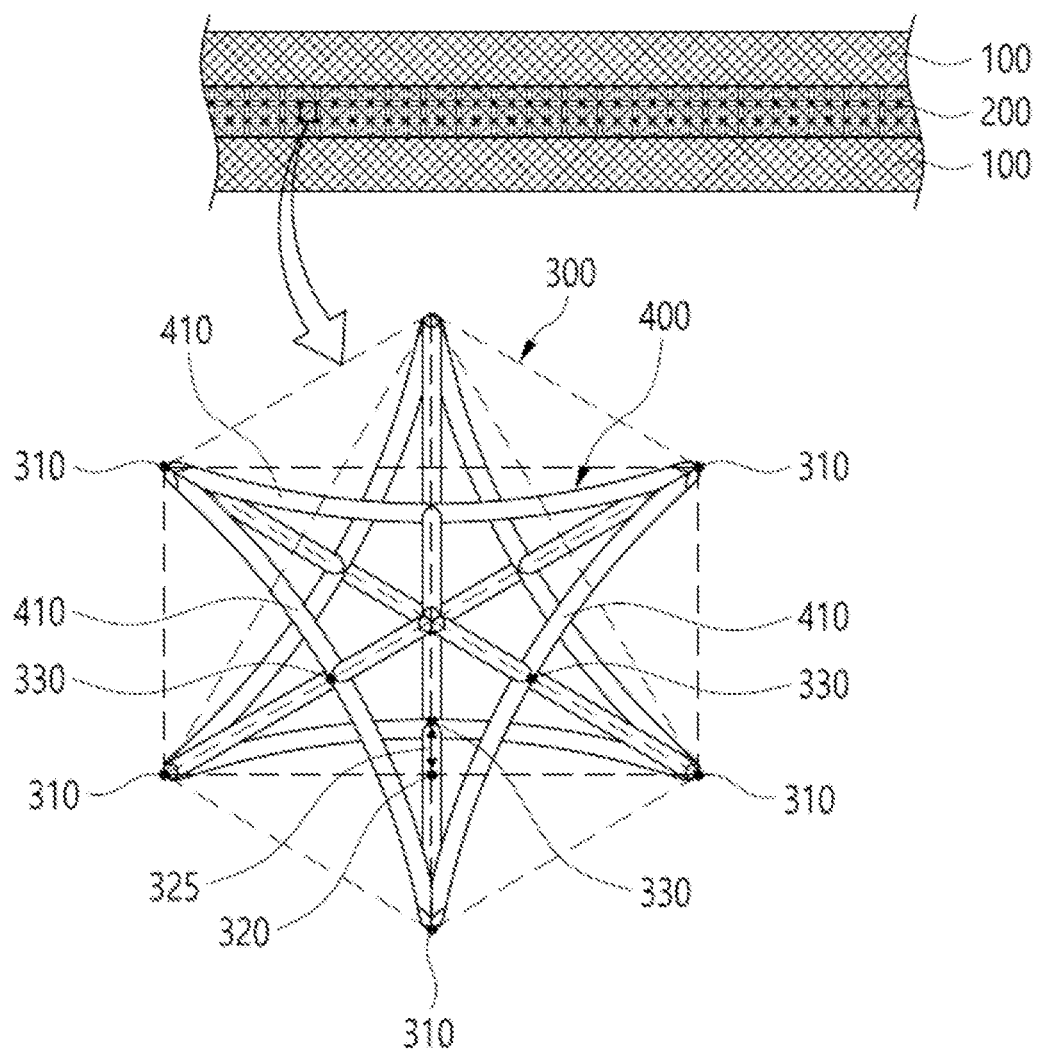
FIG. 4 is a view schematically illustrating an elastic unit body of the sidewall portion in the spinal cage according to an embodiment of the present disclosure.
Figure 5:
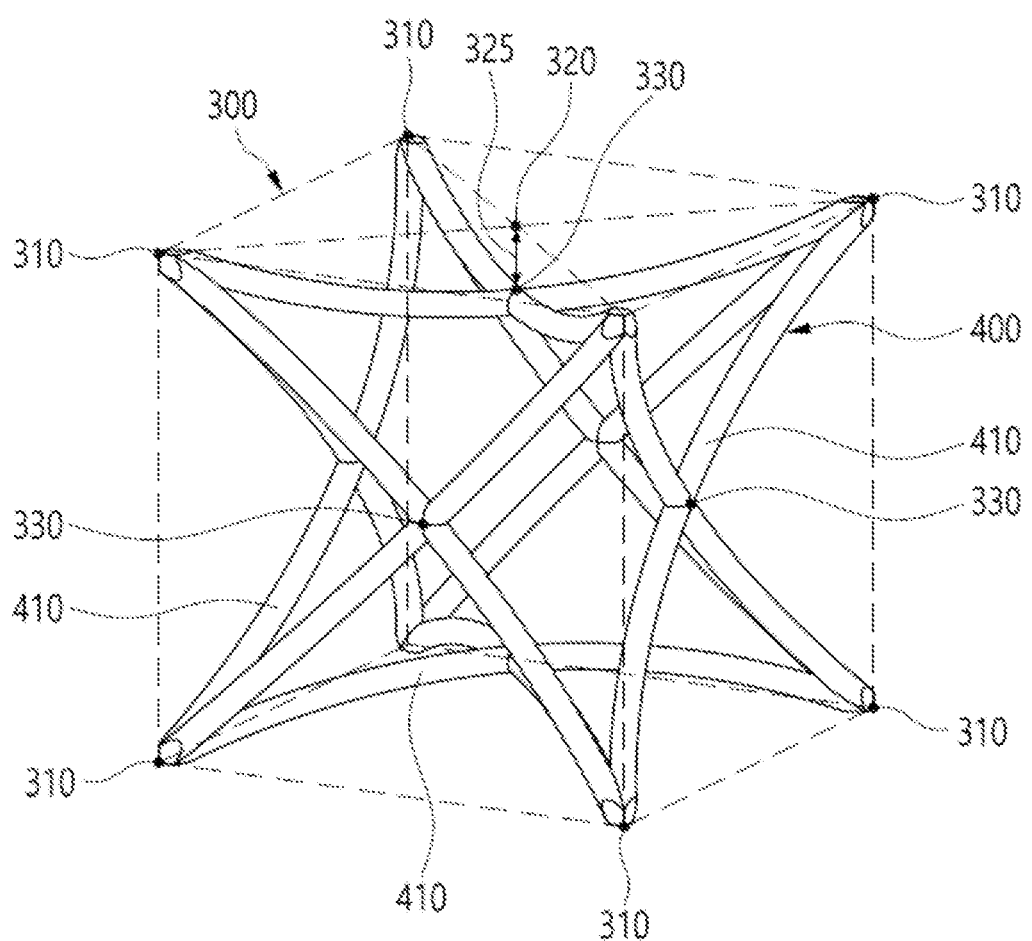
FIG. 5 is a view schematically illustrating the elastic unit body in the spinal cage according to an embodiment of the present disclosure.

FIG. 4 is a view schematically illustrating an elastic unit body of the sidewall portion in the spinal cage according to an embodiment of the present disclosure, and FIG. 5 is a view schematically illustrating the elastic unit body in the spinal cage according to an embodiment of the present disclosure.

Referring to FIGS. 4 and 5, as illustrated in FIG. 4, a plurality of elastic unit bodies 400 are formed by being consecutively arranged on the elastic band 200 of the sidewall portion.

That is, the elastic band 200 may be an assembly formed by a consecutive connection of the plurality of elastic unit bodies 400 which are elastically deformable corresponding to an external force.

Here, the elastic unit body 400 may be deformed according to an external force and may include a plurality of struts 410 connecting vertices 310 and crossing points 330 of a virtual hexahedron 300 indicated by dotted lines in the drawings.

Here, the crossing points 330 are points 330 provided at positions spaced apart at predetermined intervals 325 inward of the virtual hexahedron 300 at a face-centered 320 of the virtual hexahedron 300.

Also, in the elastic unit body 400, the strut 410 connecting a single vertex 310 and a single crossing point 330 may have an arch shape or a curved shape. The strut 410 is connected in a form of being connected to another neighboring strut 410 via a vertex 310 or a crossing point 330. The elastic unit body 400 includes the plurality of struts 410.

The elastic unit body 400 formed as above relieves pressure by causing deformation that bends the strut 410 when pressure is applied between vertebrae. Therefore, the elastic band 200 formed by the elastic unit bodies 400 being consecutively arranged may absorb the pressure applied between the vertebrae. Thus, it becomes possible to suppress an occurrence of subsidence into the vertebrae.

Figure 6:
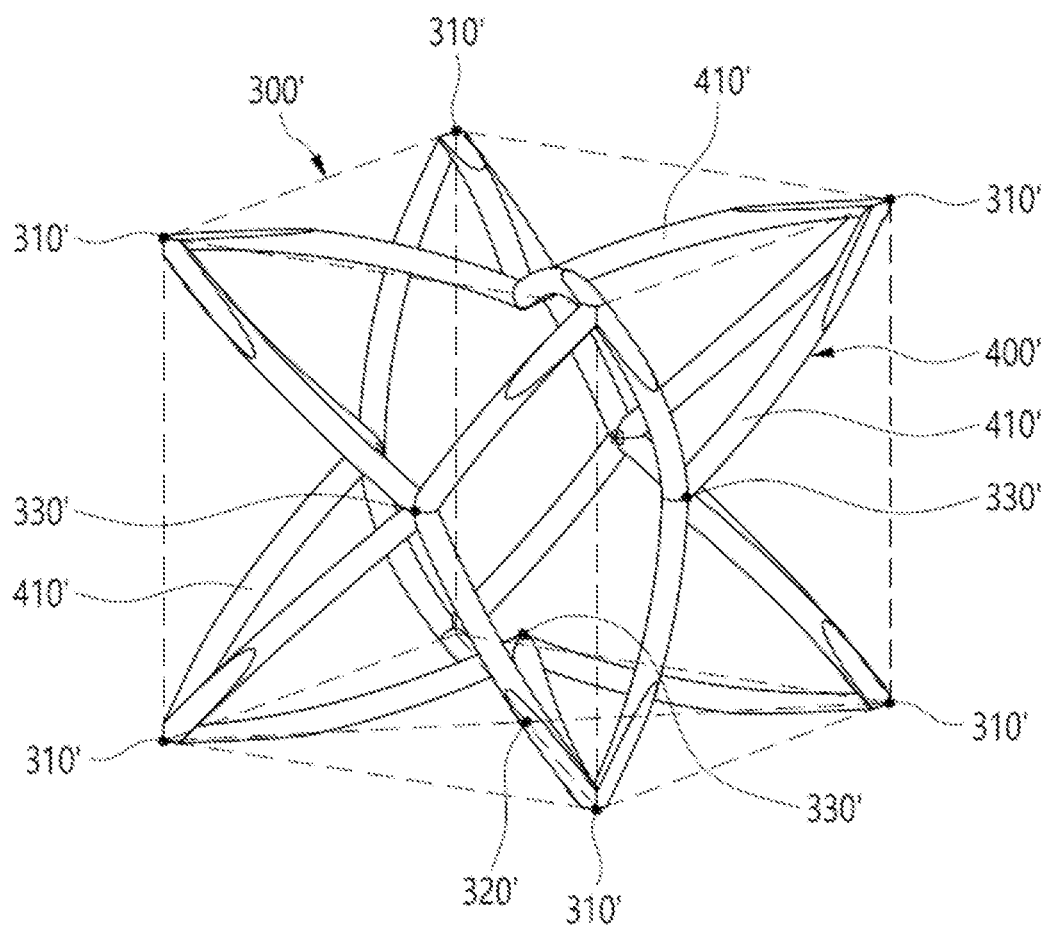
FIG. 6 is a view schematically illustrating a modified form of the elastic unit body in the spinal cage according to an embodiment of the present disclosure.

Also, the elastic unit body may also have a form illustrated in FIG. 6.

FIG. 6 is a view schematically illustrating a modified form of the elastic unit body in the spinal cage according to an embodiment of the present disclosure.

An elastic unit body 400' which can be seen from FIG. 6 is substantially the same as the elastic unit body 400 described above with reference to FIG. 5 but is slightly different therefrom in terms of an arch shape of struts 410'.

That is, the struts 410 of the elastic unit body 400 which can be seen from FIG. 5 are formed in an arch shape that is convex toward an inner side of the virtual hexahedron 300 indicated by dotted lines. Also, the struts 410' of the elastic unit body 400' which can be seen from FIG. 6 have an arch shape that is convex toward an outer side of a virtual hexahedron 300' indicated by dotted lines.

Also, the elastic unit body 400' includes a plurality of struts 410' connecting vertices 310' and crossing points 330' of the virtual hexahedron 300' indicated by dotted lines in FIG. 6. Further, as described above, the strut 410' is connected in a form of being connected to another neighboring strut 410' via a vertex 310' or a crossing point 330'.

In this way, by the strut 410 having an arch shape that is convex toward the inside as can be seen from FIG. 5 or the strut 410' having an arch shape that is convex toward the outside as can be seen from FIG. 6, the struts 410 and 410' can be elastically deformed corresponding to pressure between vertebrae, and thus the elastic unit bodies 400 and 400' can elastically absorb or relieve the pressure between the vertebrae.

Meanwhile, an elastic unit body having another form as follows is also possible.

Figure 7:
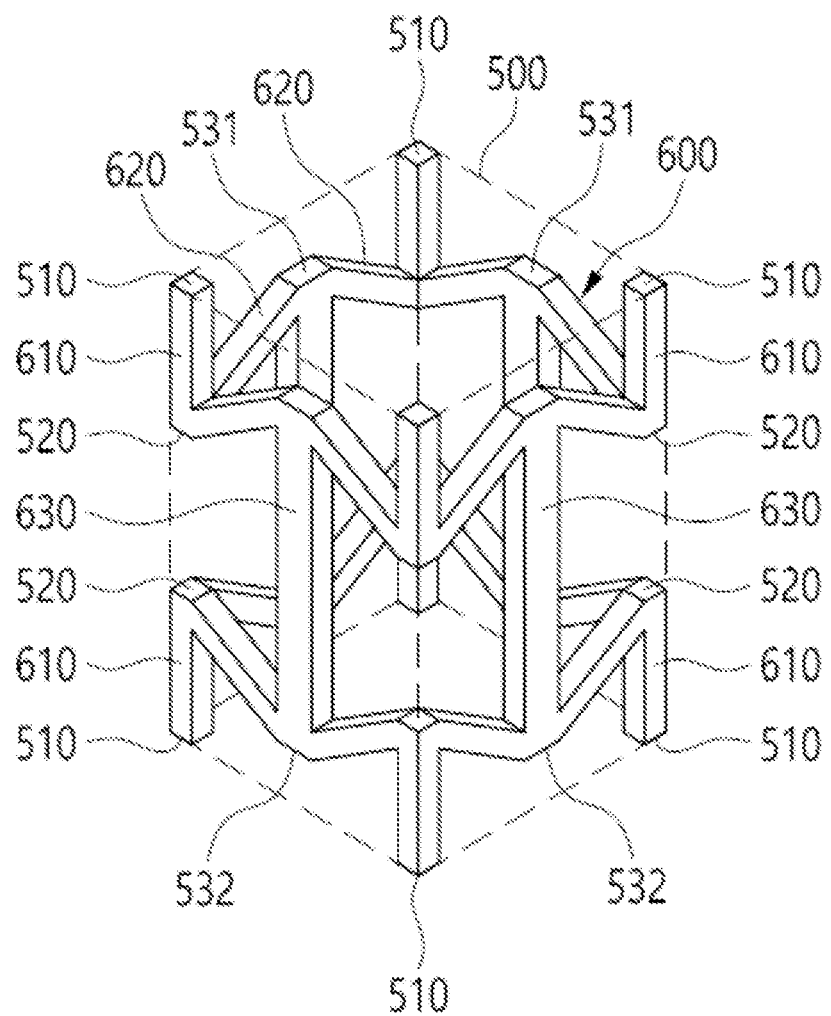
FIG. 7 is a view schematically illustrating another form of the elastic unit body in the spinal cage according to an embodiment of the present disclosure.

FIG. 7 is a view schematically illustrating another form of the elastic unit body in the spinal cage according to an embodiment of the present disclosure.

An elastic unit body 600 which can be seen from FIG. 7 includes a base beam 610, an impact absorbing beam 620, and a support beam 630.

Here, the base beam 610 has one side end positioned on a vertex 510 of a virtual hexahedron 500 indicated by dotted lines in the drawing and is formed to have a predetermined length in a height direction.

A plurality of base beams 610 are provided in a single elastic unit body 600.

A plurality of base beams 610 are provided in a single elastic unit body 600. The base beams 610 are connected to other neighboring elastic unit bodies 600 and mostly serve to provide support. Therefore, the base beams 610 may allow an external force to be distributed to a plurality of elastic unit bodies 600.

Also, as can be seen from the drawing, the impact absorbing beam 620 has one side end connected to the other side end 520 of the base beam 610, forms an acute angle relative to the base beam 610, and is formed to have a predetermined length. The impact absorbing beam 620 mostly serves to absorb impact corresponding to an external force in the elastic unit body 600.

The support beam 630 has one side end 531 connected to the other side end of the impact absorbing beam 620 and the other side end 532 connected to one side end of another impact absorbing beam 620 to have a predetermined length and has a longitudinal direction parallel to the base beam 610. The support beam 630 mostly serves to provide support in the elastic unit body 600.

Also, the base beam 610, the impact absorbing beam 620, and the support beam 630 are provided as a plurality of base beams 610, a plurality of impact absorbing beams 620, and a plurality of support beams 630 in a single elastic unit body 600.

As an angle between the base beam 610 and the impact absorbing beam 620 changes when pressure is applied between vertebrae, the elastic unit body 600 may relieve or absorb pressure between vertebrae. Alternatively, the elastic unit body 600 may relieve or absorb pressure between vertebrae by deformation that causes the base beams 610, the impact absorbing beams 620, and the support beams 630 to become close to one another.

Also, an elastic unit body having another form as follows is also possible.

Figure 8:
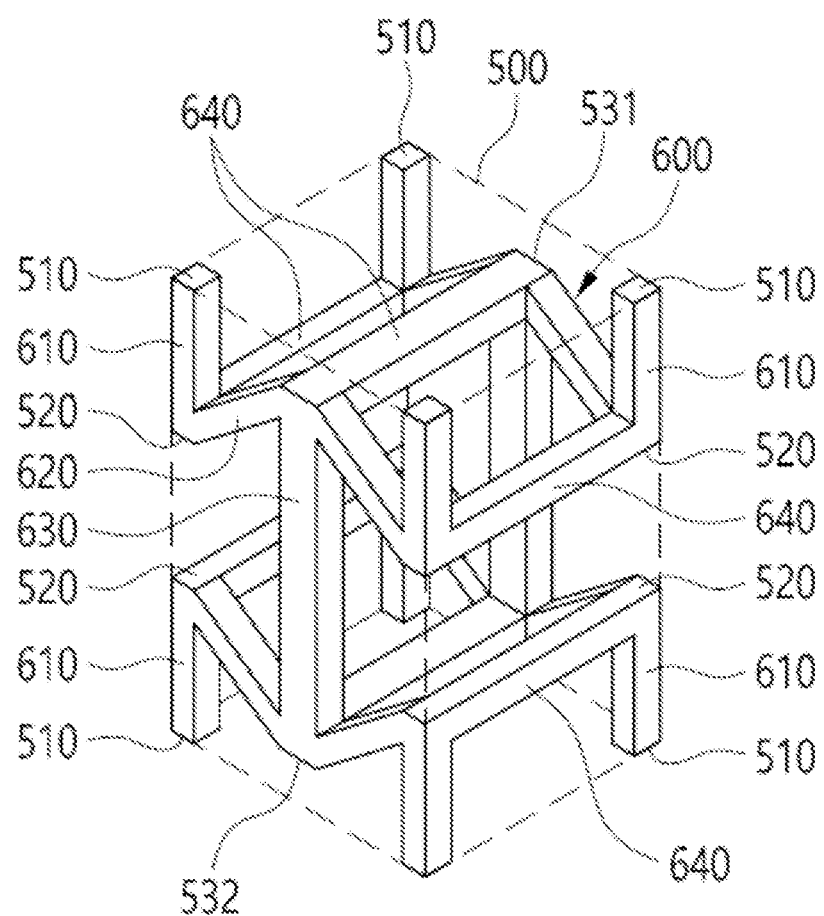
FIG. 8 is a view schematically illustrating still another form of the elastic unit body in the spinal cage according to an embodiment of the present disclosure.

FIG. 8 is a view schematically illustrating still another form of the elastic unit body in the spinal cage according to an embodiment of the present disclosure. An elastic unit body 600 which can be seen from FIG. 8 includes a base beam 610, an impact absorbing beam 620, a support beam 630, and a torsion beam 640.

The base beam 610 has one side end positioned on a vertex 510 of a virtual hexahedron 500 indicated by dotted lines in the drawing and is formed to have a predetermined length in a height direction.

A plurality of base beams 610 are provided in a single elastic unit body 600. The base beams 610 are connected to other neighboring elastic unit bodies 600 and mostly serve to provide support. Therefore, the base beams 610 may allow an external force to be distributed to a plurality of elastic unit bodies 600.

Also, as can be seen from the drawing, the impact absorbing beam 620 has one side end connected to the other side end 520 of the base beam 610, forms an acute angle relative to the base beam 610, and is formed to have a predetermined length. The impact absorbing beam 620 mostly serves to absorb impact corresponding to an external force in the elastic unit body 600.

The support beam 630 has one side end 531 connected to the other side end of the impact absorbing beam 620 and the other side end 532 connected to one side end of another impact absorbing beam 620 to have a predetermined length and has a longitudinal direction parallel to the base beam 610.

The support beam 630 mostly serves to provide support in the elastic unit body 600.

The torsion beam 640 is formed to have a predetermined length in a direction perpendicular to a longitudinal direction of the base beam 610 or the longitudinal direction of the support beam 630. Also, the torsion beam 640 is formed in a form in which one side end is connected to the other side end 520 of the base beam 610 and the other side end is connected to one side end 520 of another neighboring base beam 610 or a form in which one side end is connected to the one side end 531 of the support beam 630 and the other side end is connected to one side end 532 of another support beam 630.

As an angle between the base beam 610 and the impact absorbing beam 620 changes when pressure is applied between vertebrae, the elastic unit body 600 may relieve or absorb pressure between vertebrae. Alternatively, the elastic unit body 600 may relieve or absorb pressure between vertebrae by deformation that causes the base beams 610, the impact absorbing beams 620, and the support beams 630 to become close to one another.

Also, the torsion beam 640 may suppress or mitigate distortion of the elastic unit body 600 due to an external force.

Further, the base beam 610, the impact absorbing beam 620, the support beam 630, and the torsion beam 640 are provided as a plurality of base beams 610, a plurality of impact absorbing beams 620, a plurality of support beams 630, and a plurality of torsion beams 640 in a single elastic unit body 600.

Figure 9:
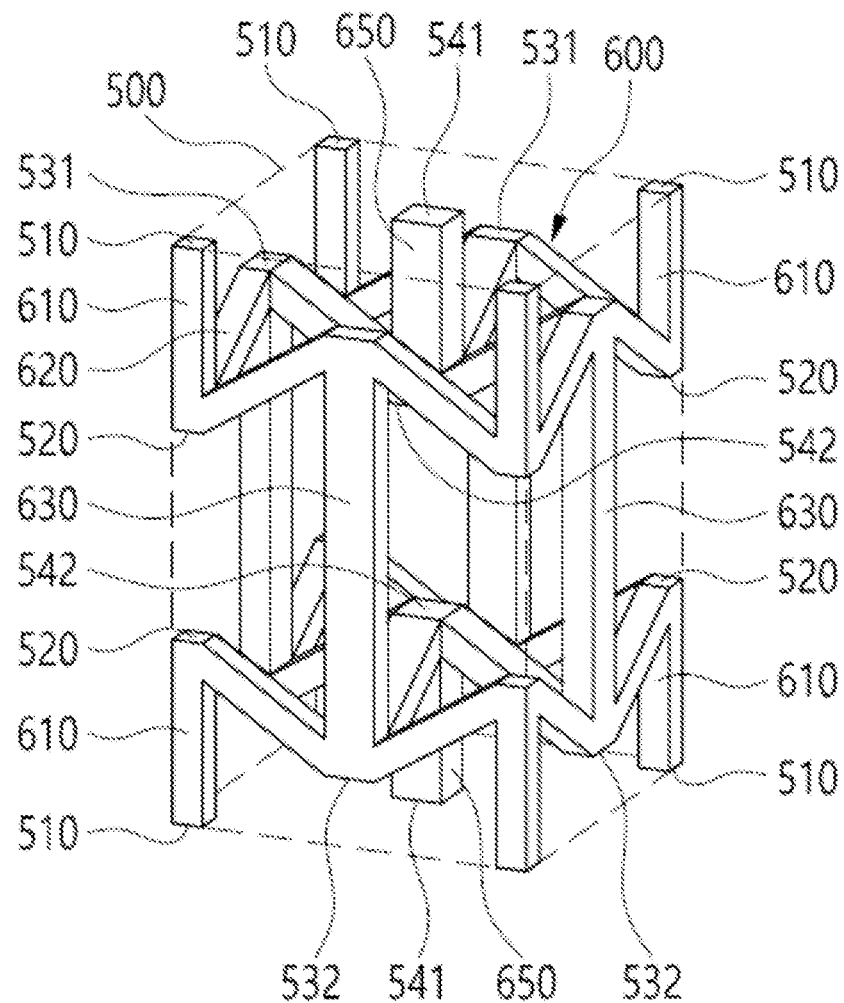
FIG. 9 is a view schematically illustrating an applied form of the elastic unit body in the spinal cage according to an embodiment of the present disclosure.

Also, an elastic unit body which can be seen from FIG. 9 is also possible.

FIG. 9 is a view schematically illustrating an applied form of the elastic unit body in the spinal cage according to an embodiment of the present disclosure. An elastic unit body 600 which can be seen from FIG. 9 includes a base beam 610, an impact absorbing beam 620, and a support beam 630.

The base beam 610 has one side end positioned on a vertex 510 of a virtual hexahedron 500 indicated by dotted lines and is formed to have a predetermined length in a height direction.

Also, one side end of a base beam 650 may be positioned at a face-centered 541 of an upper side surface or a lower side surface in the virtual hexahedron 500 indicated by dotted lines.

Also, another base beam 650 is provided at a lower side perpendicular to the above base beam 650 with a predetermined interval apart therefrom and has one side end positioned at the face-centered 541 of the lower side surface.

The base beams 610 and 650 are provided as a plurality of base beams 610 and 650 in a single elastic unit body 600. The base beams 610 and 650 are connected to other neighboring elastic unit bodies 600 and mostly serve to provide support. Therefore, the base beams 610 and 650 may allow an external force to be distributed to a plurality of elastic unit bodies 600.

Also, as can be seen from the drawing, the impact absorbing beam 620 has one side end connected to the other side end 520 of the base beam 610, forms an acute angle relative to the base beam 610, and is formed to have a predetermined length. The impact absorbing beam 620 mostly serves to absorb impact corresponding to an external force in the elastic unit body 600.

The support beam 630 has one side end 531 connected to the other side end of the impact absorbing beam 620 and the other side end 532 connected to one side end of another impact absorbing beam 620 to have a predetermined length and has a longitudinal direction parallel to the base beam 610.

The support beam 630 mostly serves to provide support in the elastic unit body 600.

In this way, as an angle between the base beam 610 and the impact absorbing beam 620 changes when pressure is applied between vertebrae, the elastic unit body 600 which can be seen from FIG. 9 may also relieve or absorb pressure between vertebrae. Alternatively, the elastic unit body 600 may relieve or absorb pressure between vertebrae by deformation that causes the base beams 610, the impact absorbing beams 620, and the support beams 630 to become close to one another.

As described above, according to a spinal cage according to the present disclosure, the overall stiffness of the spinal cage can be formed to be lower than bone stiffness, and pressure between vertebrae may be absorbed or relieved to suppress an occurrence of subsidence.

As described above, detailed description of the present disclosure has been given using embodiments with reference to the accompanying drawings. However, since the above-described embodiments are only exemplary embodiments of the present disclosure, the present disclosure should not be understood as being limited to the above embodiments, and the scope of the present disclosure should be understood as being defined by the claims below and their equivalents.

[Description of reference numerals]

| | |
|---|---|
| 10: spinal cage | 13: bone support portion |
| 15: base portion | 17: sidewall portion |
| 100, 110, 120: inelastic band | 200: elastic band |
| 100, 600: elastic unit body | 410, 410': strut |
| 610: base beam | 620: impact absorbing beam |
| 630: support beam | |

The invention claimed is:

1. A spinal cage comprising:
a bone support portion configured to be disposed between a first vertebra at an upper side and a second vertebra at a lower side, which neighbor each other, to support the first vertebra;
a base portion positioned at a lower side of the bone support portion and configured to be disposed between the first vertebra and the second vertebra to come in contact with the second vertebra; and
a sidewall portion including:
an upper side end connected to an edge of the bone support portion;
a lower side end connected to an edge of the base portion to support the bone support portion relative to the base portion; and
an elastic band positioned between a first inelastic band and a second inelastic band, the elastic band being elastically deformable in response to a pressure between the first vertebra and the second vertebra,
wherein the first inelastic band has an upper side connected to the edge of the bone support portion and a lower side connected to the elastic band, and the second inelastic band has an upper side connected to the elastic band and a lower side connected to the edge of the base portion,
wherein the first and second inelastic bands have lower elasticity than the elastic band or no elasticity,
wherein a cross-sectional thickness of the elastic band gradually increases from a center thereof toward an edge thereof, and
wherein the elastic band comprises a plurality of elastic unit bodies arranged in series, the elastic unit bodies being elastically deformable in response to an external force.

2. The spinal cage of claim 1, wherein the first inelastic band and the second inelastic band are formed so that elasticity gradually decreases from the elastic band toward the bone support portion or the base portion.

3. The spinal cage of claim 1, wherein:
each of the plurality of elastic unit bodies is deformable according to the external force and includes a plurality of struts connecting vertices and crossing points of a virtual hexahedron; and
the crossing points are points provided at positions spaced apart at predetermined intervals inward of the virtual hexahedron at a face-centered of the virtual hexahedron.

4. The spinal cage of claim 3, wherein each of the plurality of struts has an arch shape or a curved shape.

5. The spinal cage of claim 1, wherein each of the plurality of elastic unit bodies includes:
a base beam which has one side end positioned on a vertex of a virtual hexahedron and has a predetermined length in a height direction;
an impact absorbing beam which has one side end connected to the other side end of the base beam, forms an acute angle relative to the base beam, and has a predetermined length; and
a support beam which has one side end connected to the other side end of the impact absorbing beam and the other side end connected to one side end of another impact absorbing beam to have a predetermined length and which has a longitudinal direction parallel to the base beam.

6. The spinal cage of claim 1, wherein each of the plurality of elastic unit bodies includes:
a base beam which has one side end positioned on a vertex of a virtual hexahedron and has a predetermined length in a height direction;
an impact absorbing beam which has one side end connected to the other side end of the base beam, forms an acute angle relative to the base beam, and has a predetermined length;
a support beam which has one side end connected to the other side end of the impact absorbing beam and the other side end connected to one side end of another impact absorbing beam to have a predetermined length and which has a longitudinal direction parallel to the base beam, and
a torsion beam having a predetermined length in a direction perpendicular to a longitudinal direction of the base beam or the longitudinal direction of the support beam,
wherein the torsion beam has one side end connected to the other side end of the base beam and the other side end connected to one side end of another base beam or has one side end connected to the one side end of the support beam and the other side end connected to one side end of another support beam.

* * * * *